US012016569B2

(12) United States Patent
Buchbinder

(10) Patent No.: US 12,016,569 B2
(45) Date of Patent: Jun. 25, 2024

(54) LEFT ATRIAL APPENDAGE OCCLUSION METHODS AND DEVICES

(71) Applicant: Maurice Buchbinder, San Diego, CA (US)

(72) Inventor: Maurice Buchbinder, San Diego, CA (US)

(*) Notice: Subject to any disclaimer, the term of this patent is extended or adjusted under 35 U.S.C. 154(b) by 491 days.

(21) Appl. No.: 16/629,332

(22) PCT Filed: Jul. 10, 2018

(86) PCT No.: PCT/US2018/041436
§ 371 (c)(1),
(2) Date: Jan. 8, 2020

(87) PCT Pub. No.: WO2019/014219
PCT Pub. Date: Jan. 17, 2019

(65) Prior Publication Data
US 2021/0137528 A1 May 13, 2021

Related U.S. Application Data

(60) Provisional application No. 62/682,443, filed on Jun. 8, 2018, provisional application No. 62/530,669, filed on Jul. 10, 2017.

(51) Int. Cl.
*A61B 17/12* (2006.01)

(52) U.S. Cl.
CPC .... *A61B 17/12122* (2013.01); *A61B 17/1204* (2013.01); *A61B 17/12136* (2013.01)

(58) Field of Classification Search
CPC .......... A61B 17/1204; A61B 17/12122; A61B 17/12136; A61B 2017/1205; A61B 2017/0065; A61M 5/007
See application file for complete search history.

(56) References Cited

U.S. PATENT DOCUMENTS

| 7,566,336 | B2* | 7/2009 | Corcoran | A61B 17/12122 606/151 |
| 8,647,367 | B2* | 2/2014 | Kassab | A61M 29/02 604/509 |
| 9,011,551 | B2* | 4/2015 | Oral | A61N 1/37205 623/23.72 |
| 9,795,387 | B2* | 10/2017 | Miles | A61B 17/1219 |
| 10,667,896 | B2* | 6/2020 | Delaney, Jr. | A61B 17/12145 |
| 10,893,926 | B2* | 1/2021 | VanTassel | A61B 17/0057 |
| 2005/0113861 | A1* | 5/2005 | Corcoran | A61B 17/0057 606/200 |
| 2006/0052816 | A1* | 3/2006 | Bates | A61B 17/12022 606/200 |

(Continued)

*Primary Examiner* — Ryan J. Severson
(74) *Attorney, Agent, or Firm* — John M. Berns

(57) ABSTRACT

Left atrial occlusion devices and methods of implantation. The left atrial occlusion devices can have a plurality of flexible elongate members forming a distally open cage configuration when expanded. The distal ends of the elongate members can optionally be atraumatic. Also disclosed is a method of occluding a left atrial appendage that includes expanding an expandable member against the left atrial appendage to seal off the left atrial appendage from blood flow from the left atrium, and determining if blood is flowing from within the left atrial appendage to a location outside the left atrial appendage.

9 Claims, 4 Drawing Sheets

(56) References Cited

U.S. PATENT DOCUMENTS

| | | | |
|---|---|---|---|
| 2010/0191279 A1* | 7/2010 | Kassab | A61B 17/12031 606/213 |
| 2012/0283585 A1* | 11/2012 | Werneth | A61P 9/06 606/200 |
| 2013/0018413 A1* | 1/2013 | Oral | A61B 17/12186 606/213 |
| 2015/0066074 A1* | 3/2015 | Miles | A61B 17/1219 606/200 |
| 2016/0058539 A1* | 3/2016 | VanTassel | A61B 17/12122 606/200 |
| 2016/0089151 A1* | 3/2016 | Siegel | A61B 17/12122 606/194 |
| 2016/0192911 A1* | 7/2016 | Kassab | A61B 1/00165 606/200 |
| 2017/0135801 A1* | 5/2017 | Delaney, Jr. | A61B 17/12122 |
| 2019/0175191 A1* | 6/2019 | Min | A61B 17/12122 |
| 2021/0137528 A1* | 5/2021 | Buchbinder | A61B 17/00491 |
| 2022/0265280 A1* | 8/2022 | Chamorro | A61B 17/12172 |
| 2023/0329722 A1* | 10/2023 | Buchbinder | A61B 17/12031 |

\* cited by examiner

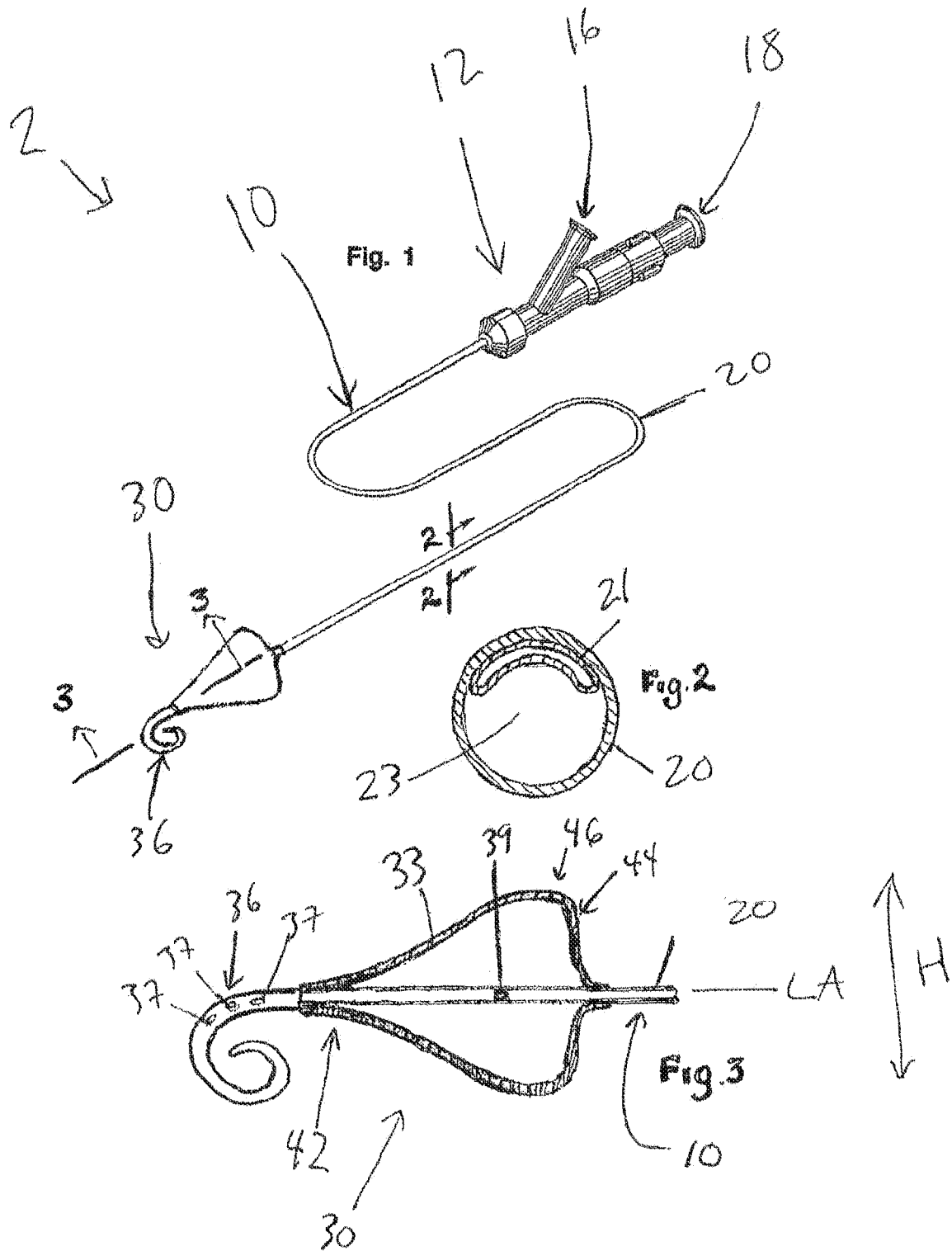

LEFT ATRIAL APPENDAGE OCCLUSION METHODS AND DEVICES

CROSS REFERENCE TO RELATED APPLICATIONS

This application claims priority to the following U.S. Provisional Applications, the disclosures of which are incorporated by reference herein: U.S. Prov. App. No. 62/530,669, filed Jul. 10, 2017, and U.S. Prov. App. No. 62/682,443, filed Jun. 8, 2018.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The left atrial appendage ("LAA") is a small sac in the muscle wall of the left atrium. It is unclear what function, if any, the LAA performs. In normal hearts, the heart contracts with each heartbeat, and the blood in the left atrium and LAA is squeezed out of the left atrium into the left ventricle.

Atrial fibrillation (AF) is the irregular, chaotic beating of the upper chambers of the heart. Electrical impulses discharge so rapidly that the atrial muscle quivers or fibrillates. When a patient has atrial fibrillation, the electrical impulses that control the heartbeat do not travel in an orderly fashion through the heart. Instead, many impulses begin at the same time and spread through the atria. The fast and chaotic impulses do not give the atria time to contract and/or effectively squeeze blood into the ventricles. Because the LAA is a little pouch, blood collects there and can form clots in the LAA and atria. When blood clots are pumped out of the heart, they can cause a stroke.

It is estimated that AF patients have five times the stroke risk of patients without AF. Most AF patients, regardless of the severity of their symptoms or frequency of episodes, require treatment to reduce the risk of stroke. In non-valvular AF, over 90% of stroke-causing clots that come from the left atrium are formed in the LAA.

The most common treatment for stroke risk reduction in patients with AF is blood-thinning warfarin therapy. Warfarin and other approved oral anticoagulants effectively reduce the risk of cardioembolic stroke and are the most commonly used treatments in at-risk patients with non-valvular atrial fibrillation. Many patients have concerns about, or dislike, taking warfarin. Some of the reasons for this are: Frequent blood draws are needed to measure the patient's international normal ratio (INR), or clotting time. The tests are needed to make sure the patient takes the right amount of medication; while taking warfarin, you need to limit your intake of certain foods that contain vitamin K; the risk of bleeding is higher while taking warfarin; and some patients do not tolerate warfarin or have trouble maintaining a normal INR.

There has thus been a desire to attempt to filter, occlude and/or isolate the LAA to prevent clots from forming therein, which can be subsequently released from the LAA and cause a stroke. It is also desirable to occlude the LAA to isolate blood clots that may already be forming in the left atrial appendage.

There are devices on the market that are adapted to filter and/or occlude the LAA to reduce the likelihood of stroke. For example, the Watchman™ device (FDA approved in 2015) is implanted in the left atrial appendage, and initially acts as a filter between the LAA and the atria to prevent clots from being released from the LAA. Over time, cells grow over the device, effectively sealing off the LAA from the atrium. US Publication 2016/0058539, including all of its methods of delivering an occlusion device to the LAA, are incorporated by reference herein.

There is a need to modified and improved occlusion devices, and devices and methods of implantation are described herein.

The LAA is a very delicate appendage, and it can rupture during the implantation procedure of LAA occlusion devices. During a transeptal approach for deploying the Watchman™ or similar devices, a guidewire is positioned in the LAA to enable proper placement of an access sheath. A delivery system, including the implantable device, is delivered through the access sheath and into position at the ostium of the LAA. Without intending to be limiting, the LAA can rupture when the guidewire is advanced into the LAA (i.e., due to inadvertent over-manipulation of LAA tissue with the guidewire), or during expansion and implantation of the implantable device (i.e., as the implant contacts the LAA tissue). LAA rupture occurs in about 1-3% of the procedures. LAA rupture is effectively a rupture of the heart, and thus bloods immediately begins to leak out of the heart, which amounts to a catastrophic failure, generally leading to patient death within moments. There is no way to stop the bleeding out of the heart during the procedure, and thus the access sheath and delivery system must immediately be withdrawn, and the patient must immediately be sent to the operating room, where a surgeon is on standby. Every time a LAA implantation procedure is performed, both an operating room and a surgeon must be on standby in case of a LAA rupture, which adds to the cost of the procedure.

While LAA rupture only occurs in about 1-3% of the procedures, the result is almost always patient death. And given the preventative nature of the procedure (i.e., to reduce the likelihood of future stroke), the patient must make a difficult decision when deciding whether to have the procedure or not. Not having the procedure maintains their 5× likelihood of having a stroke, but having the procedures comes with a 1-3% chance of a catastrophic failure leading to almost certain death.

Methods and device are also needed that will increase the safety of LAA implant procedures in the event of a catastrophic failure such as LAA rupture.

SUMMARY OF THE DISCLOSURE

One aspect of the disclosure is a method of occluding a left atrial appendage ("LAA), comprising: expanding an expandable member, such as an expandable membrane, of an occlusion device against LAA tissue, LAA ostium tissue, and/or left atrium tissue adjacent a LAA ostium in an attempt to seal off the LAA from blood flow from the left atrium; and optionally determining if blood if flowing from within the LAA to a location outside the LAA.

The method can also include delivering the expandable member through a lumen (optionally an access sheath lumen) that was previously positioned in the left atrium as part of a procedure attempting to deliver a LAA implantable occlusion or closure device.

If included, the determining step can comprise injecting a dye into the LAA and visualizing the dye to determine if the dye is moving from a location inside the LAA to outside the LAA, which indicates the existence of a leak in the LAA.

The method may further include sealing a ruptured opening in LAA tissue. Sealing a ruptured opening in the LAA can comprise injecting a sealant into the LAA to seal off the ruptured opening in the LAA. Injecting a sealant into the LAA can comprise injecting a sealant out of the occlusion device. Injecting a sealant out of the occlusion device can comprise injecting a sealant out of at least one aperture in the occlusion device, wherein the at least one aperture is distal to an expandable member. After attempting to seal a ruptured opening in the LAA, the method can also include injecting dye into the LAA and visualizing the dye to determine if the dye is moving from a location inside the LAA to a location outside of the LAA, which indicates the continued existence of a leak in the LAA.

Expanding an expandable member may comprise temporarily expanding an expandable member, or permanently expanding an expandable member.

Expanding the expandable member can comprise delivering a predetermined volume of inflation fluid into the expandable member to inflate the expandable member.

Expanding the expandable member can comprise expanding the expandable member until it assumes a pre-set configuration, optionally a pear configuration.

The method can further comprise advancing a curved distal member of the device into the LAA until resistance is felt.

Expanding an expandable member can comprise expanding a plurality of elongate members of the occlusion device against LAA tissue, LAA ostium tissue, and/or left atrium tissue adjacent a LAA ostium, and optionally wherein at least one of the plurality of elongate members has an atraumatic distal end. Expanding the plurality of elongate members can comprise inflating a balloon within the plurality of elongate members and urging the plurality of elongate radially outward and toward tissue. Inflating a balloon can comprise inflating a balloon with a predetermined shape when inflated with a known volume. Inflating a balloon can comprise inflating a balloon with a predetermined configuration upon full expansion that tapers generally in the distal direction. The method can further comprise deflating the balloon and removing it from the patient, while leaving the occlusion device within the patient. Removing the balloon can comprise removing the balloon through a portion of the occlusion device, optionally a central region.

Expanding an expandable member can comprise expanding a plurality of tines. Expanding the plurality of elongate members can cause at least one hook or barb (or other tissue piercing element) that is carried by one of the plurality of elongate members to pierce or securely engage appendage tissue and help stabilize the occlusion device with respect to the left atrial appendage, and optionally wherein each elongate member carries at least one hook or barb (or other tissue piercing element), and wherein expanding the elongate members can cause all of the hooks or barbs (or or other tissue piercing elements) to pierce appendage tissue.

The method can also include releasing the occlusion device from a delivery device, and removing the delivery device from the patient while leaving the occlusion device expanded in place.

One aspect of the disclosure is a left atrial appendage ("LAA") occlusion device, comprising: an expandable member (optionally comprising an expandable membrane) carried by an elongate member; an inflation aperture within the expandable member and in communication with the interior of the expandable member to allow an inflation fluid to be advanced into the expandable member to inflate the expandable element; and a second aperture to allow at least one of a dye or a sealant to be delivered out of the second aperture and into the LAA.

The expandable member can have a general pear shape.

The expandable member can have a height, and a greatest height of the device can be in a proximal portion of the expandable member. The expandable member can taper downward from a location with the greatest height towards a distal end of the expandable member.

The device can also include a distal member extending distally from the expandable member.

The distal member can comprise a curved configuration, optionally a pig-tail configuration. The distal member can comprises the second aperture.

The device can be sized and configured to be advanced within a 14F access sheath or guiding catheter.

The expandable member can comprise a membrane with a pre-set manufactured configuration.

The expandable member can comprise a membrane with a pre-set configuration that is adapted to assume the pre-set configuration when inflated with a predetermined volume of inflation fluid (e.g., liquid or gas).

The expandable member can comprise a membrane that comprises silicone. The expandable member can comprise a membrane that comprises latex. The expandable member can comprise a membrane that is elastic. The expandable member can comprise a membrane that is inelastic.

One aspect of the disclosure is an implantable device adapted for left atrial appendage occlusion, comprising: a plurality of elongate members, optionally wherein at least one of them has an atraumatic distal end.

The plurality of elongate members may not be attached at their respective distal ends. The plurality of elongate members can have proximal ends that are coupled, either directly or indirectly, to a proximal end of at least one of the other proximal ends. The plurality of elongate members may taper generally in the distal direction, and optionally which together define a general pear shape.

The plurality of elongate members can each have proximal regions that are coupled to a LAA barrier.

The plurality of elongate members can each have proximal regions that extend distally when in a non-expanded configuration, and radially inward after the implantable device is expanded.

The plurality of elongate members can each have proximal regions that are adapted to deform from a first delivery configuration to a second barrier configuration.

The plurality of elongate members may not form what is commonly known as a stent or stent-like configuration. The plurality of elongate members may not be formed by laser cutting a tubular member.

One aspect of the disclosure is a system for positioning a balloon expandable LAA occlusion device, comprising: an elongate shaft carrying an expansion balloon, the elongate shaft having an inflation lumen therein in fluid communication with an interior of the balloon; an implantable LAA occlusion device adapted to be fit over at least a portion of the balloon in a non-expanded configuration, the implantable device including a plurality of balloon expandable elongate members, the elongate members having open distal ends and proximal ends attached to a barrier.

The proximal ends can together assume or form a flatter configuration that forms a proximal region of the implant when the device is expanded.

BRIEF DESCRIPTION OF THE DRAWINGS

FIG. 1 illustrates a merely exemplary left atrial appendage occlusion system for occluding a left atrial appendage.

FIG. 2 shows a sectional view along section 2-2 shown in FIG. 1.

FIG. 3 shows a side sectional view along section 3-3 shown in FIG. 1.

DETAILED DESCRIPTION

Figure 4:
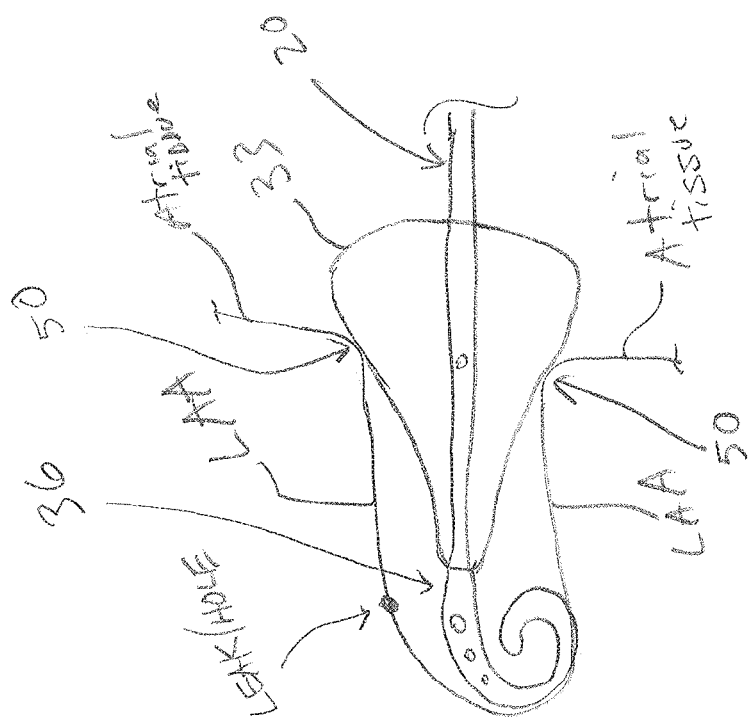
FIG. 4 shows an exemplary method of use and placement of the device from FIGS. 1-3.

The disclosure generally relates to methods and devices for occluding a left atrial appendage ("LAA"). Some aspects of the disclosure relate to implantable devices adapted, sized and configured for LAA occlusion (see, for example, FIGS. 5 and 6). Some aspects of this disclosure can be used in the event of a catastrophic failure, such as a LAA rupture (see, for example, FIGS. 1-4). Some aspects of the different embodiments herein, however, may be suitable for incorporation into different embodiments, including devices and methods.

The first part of this this disclosure generally describes devices adapted for and methods of treating a LAA rupture. A LAA rupture can be caused by a minimally invasive procedure in which an attempt is made to implant a LAA occlusion and/or closure device, such as, for example, the Watchman™ device sold by Boston Scientific, or the devices shows in FIGS. 5 and 6. Methods herein may also include, following a rupture in the LAA, sealing a hole in the LAA. The methods herein can include temporarily occluding a LAA, but in some instances the method can include a permanent occlusion of the LAA.

During the implantation of some LAA occlusion and/or closure devices, an access sheath is already in place in the atrium to facilitate delivery of the delivery system. In the event of a LAA rupture (such as caused by a guidewire or the implantable device), the guidewire or delivery system are removed from the access sheath (depending on when in the procedure the rupture occurs), leaving it available for another device to be quickly inserted through its lumen and to the LAA. The presence of a previously-placed access sheath or guiding catheter (or other access device with a lumen therein) is generally an important step in the methods herein, in that a subsequent procedure to treat the LAA rupture needs to be performed almost immediately after the rupture, and the existing access sheath or guiding catheter provides a device that facilitates delivering the necessary tools very quickly to the LAA.

After detecting a ruptured LAA, a separate occluding device can be quickly advanced through the previously placed access sheath. An expandable device, which may include an expandable membrane, can then be expanded against LAA tissue, LAA ostium tissue, or left atrium tissue adjacent a LAA ostium, in an attempt to occlude or isolate the LAA from blood flow from the left atrium. By preventing blood from the left atrium into the LAA, any leak in LAA tissue can be isolated from the left atrium to prevent further blood loss from the left atrium.

After an attempt has been made to occlude the LAA and isolate a leak from the left atrium, it can be determined if blood is flowing from within the LAA to a location outside the LAA. Using the occluding device, a dye can be injected into the LAA, followed by visualizing the dye to determine if the dye is moving from a location inside the LAA to outside the LAA, which indicates the existence of an opening (aka a leak) in the LAA. If an opening is visually detected, the method can further comprises sealing the opening. For example without limitation, sealing an opening in the LAA comprises using the device to inject a sealant into the LAA to seal off the opening in the LAA. The device can include an aperture out of which the sealant is delivered into the LAA. The sealant, which can be a wide variety of biocompatible adhesives, will seal off the opening when exposed to the tissue with the leak. After attempting to seal the opening in the LAA, dye can then be injected once again into the LAA, followed by visualization to determine if the dye is moving from a location inside the LAA to a location outside of the LAA, which indicates the continued existence of a opening in the LAA. The step of injecting adhesive can be repeated as necessary, followed by dye injection and visualization, until the opening has been sealed off. Once the opening has been effectively sealed, the patient can then be monitored for any length of time as needed.

In some embodiments the device is temporary and is removed from the patient once it is determined that the opening is sealed. In some instances, however, the device is adapted to be left in place permanently as the implantable LAA occlusive and/or closure device.

In some embodiments, the Watchman™ device can be modified such that it can perform any of the methods herein. For example, the Watchman™ delivery system could be modified to have a sealant delivery aperture, such that if a rupture occurred when the delivery system was already positioned in the left atrium and/or LAA, a sealant could be delivered from it in an attempt to seal the LAA rupture. The Watchman™ delivery system could also be modified to include a dye port to monitor leakage out of the LAA, as is described herein.

FIGS. 1-4 illustrate a merely exemplary left atrial appendage occlusion device 2 for occluding a left atrial appendage. Occlusion device 2 includes external portion 12 coupled to elongate member 10 that comprises shaft 20, and expandable member 30 carried by a distal region of shaft 20. Expandable member 30 is shown in an expanded (in this case inflated) configuration. External portion 12 includes inflation fluid port 16 and internal lumen port 18.

As can be seen in the sectional view of FIG. 2 taken along section 2-2 shown in FIG. 1, inflation fluid port 16 is in communication with inflation lumen 21, and internal lumen port 18 is in communication with main lumen 23.

LAA occlusion device 2 includes an expandable member 30 (in this embodiment including an expandable membrane 33, or balloon) carried by shaft 20 of elongate member 10, either by being directly attached to elongate member 10 or indirectly attached to elongate member 10. Distal to expandable member 30 is distal elongate member 36, which includes at least one aperture 37 therein (three apertures 37 are shown).

Elongate member 10 includes a shaft 20 and has a first lumen 21 therein in fluid communication with port 16 and inflation port 39, which is disposed inside expandable member 30. An inflation fluid can thus be delivered into port 16, down lumen 21 and out port 39 and into expandable member 30, causing the expansion (in this case inflation) of expandable member 30.

In this embodiment expandable member 30 includes a membrane 33 that has an inflated configuration configured to close off the LAA after it has been inflated. The shape is important in that the goal of inflation is to isolate any holes in the LAA from the left atrium. The membrane 33 thus optimally will seal off the LAA from the left atrium.

In this embodiment the membrane 33 has a general pear shape, with the greatest height (see Height "H" dimension shown in FIG. 3; orthogonal to longitudinal axis "LA") in a proximal region 46 of the membrane 33. When a mid-point of the length of the expandable member 30 is determined, proximal region 46 is, in this embodiment, proximal to the mid-point. The membrane tapers downward from the greatest height dimension in the distal direction. Since there is patient-to-patient variability in the shape of the LAA, the membrane's pear configuration allows it to be securely engaged against LAA or ostia regardless of the specific patient configuration and size. The membrane, once expanded, can be advanced as far distally as it needs to be in order to engage tissue and isolate the LAA. The isolation step is critical to stabilize the blood leakage out of the heart. Membrane 33 has a configuration that allows it to be expanded so as to snugly fit against the LAA or at the location of the ostia, and isolate the LAA.

In preferred embodiments (but not limiting), the membrane is manufactured to have a particular configuration at maximum volume. That is, when the membrane is inflated with a known volume of fluid (air or liquid), the membrane will assume the pre-set, or manufactured configuration. This allows the membrane to always assume the desired configuration when inflated inside the patient's LAA or ostium. The membrane can comprise a silicone material, such as the balloon of a Foley Catheter, whose constructions are known. The membrane can also be latex. The material of the membrane is generally very thin.

In this embodiment the expanded configuration of membrane 33 includes a proximal region 46 with a greater height than distal region 42, with the membrane tapering radially inward in the distal direction relative to proximal region 46. The expanded configuration also includes a proximal most region 44 that extends radially outward, relative to longitudinal axis LA, from the proximal end of the membrane to greatest height region 46.

The membrane is volumetric, that is, it is inflated with a known volume of fluid such that the membrane assumes the known configuration, and is not pressure related. The membrane can be inflated at relatively low pressure.

The material of the membrane can be elastic, or in some embodiments it may be generally inelastic and have a pre-set configuration with inelastic material.

The distal member 36 is distal to expandable member 30 and, in this embodiment, has a pig-tail configuration, which will naturally be able to find the end/bottom of the LAA non-traumatically. The distal member can be made from any number of flexible materials, such as a variety of polymeric materials.

Distal member 36 can be secured to elongate member 10 and/or expandable member 30 using any known securing techniques, such as adhesive bonding. Distal member 36 may also be an extension of shaft 20.

The occlusion device 2 also includes an inflation port 39 in the shaft 20, within membrane 33, that allows an inflation fluid to be delivered out of port 39, at a known volume, so membrane 33 will assume the pre-set configuration when inflated with the pre-set volume.

In an exemplary method of use, device 2 is advanced distally through a previously positioned access sheath or guiding catheter (not shown). Expandable member 30 is advanced out of a distal end of the access sheath and into the left atrium of the LAA. At this time the expandable member 30 is in an unexpanded (in this case uninflated) configuration. The device is continued to be advanced until distal member 36 is disposed within the LAA and resistance is felt.

A predetermined volume of inflation fluid is then advanced, from port 16, down inflation lumen 21, out aperture 39, and into expandable member 30 to cause membrane 33 to assume the known configuration, as is shown in FIG. 4. Inflation of the membrane causes the expandable member 30 to engage tissue at locations 50, sealing off the LAA from the left atrium. The expandable member may alternatively be inflated to max volume and then advanced distally into the LAA until the distal member engages LAA tissue.

A dye is then injected through port 18, through second lumen 23 and out one of apertures 37. The dye can be visualized under fluoroscopy to determine if it a leak exists in the LAA. If a leak is detected, a sealant is then delivered from outside the device, through the device in lumen 23, and out one of apertures 37. The sealant will seal off the detected leak. Dye is then injected through the device again and out one of apertures 37 to determine if the dye leaks out of the LAA. The sealing and dye procedure is repeated until it is determined that the leak has been sealed off and dye is no longer leaking out of the LAA.

Once the leak is sealed, the device can be removed from the patient. In some embodiments, however, the device can be adapted to be a permanent implant and is adapted to be detached from a system, similar to the Watchman™ deployment.

Figure 5:
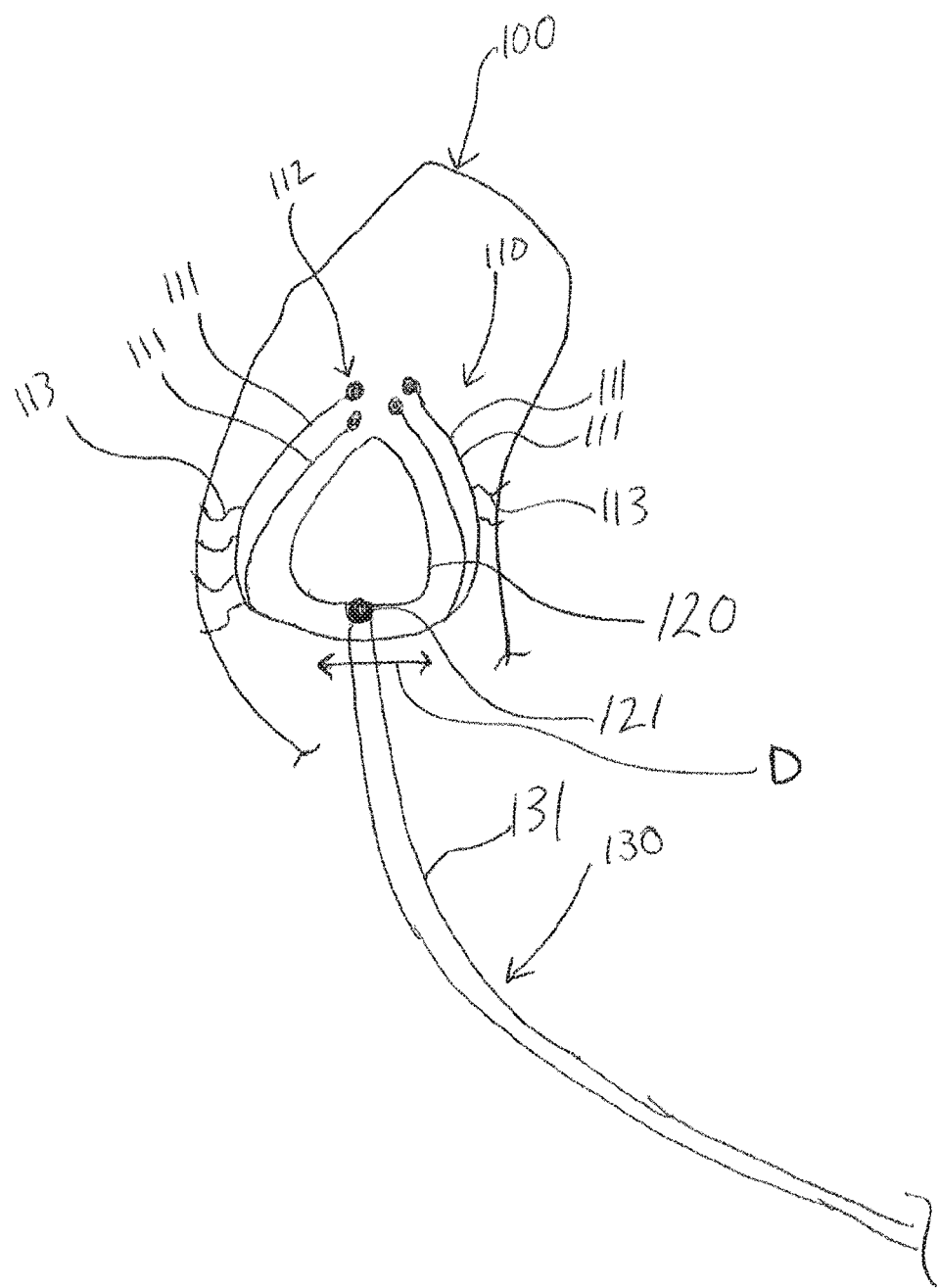
FIG. 5 shows an exemplary permanent implant adapted for occluding a LAA.

FIG. 5 illustrates a distal portion of an alternative occlusion device 110 that can be used to seal off the LAA 100 from blood flow from the left atrium, optionally in the case of an emergency situation as described above. Alternatively, device 110 can also be used in non-emergency situations, and can be used as a permanent LAA occlusion implant, rather than just temporarily placed. The delivery access routes and procedures described above can similarly apply to this embodiment as well.

The occlusion device 110 includes a plurality of expandable elongate members 111 that optionally include atraumatic distal ends 112 (only one atraumatic distal end is labeled for clarity). The expandable elongate members 111 can be in the form of elongate splines, or arms, and alternatively they could be overlapping and/or interwoven elongate members, such as a braid. Expandable elongate members 111 can be made from an elastic material, such as nitinol. In this embodiment, the elongate members 111 are not coupled to one another, or to anything else, at their distal ends (i.e., they have free distal ends, or open distal ends), and they together define an open volume radially within the elongate members 111. The elongate members can be thought of as defining an open ended cage.

The elongate members are not directly coupled to anything at their distal ends, and also are not coupled directly to anything along most of their lengths. In some embodiments the elongate members 111 are not directly coupled to anything along at least 50% of the lengths (starting at their distal ends), along at least 55% of the lengths, along at least 60% of their lengths, along at least 75% of the lengths, or more (e.g., 80%, 85%, 90%, 95% of their lengths). "Directly coupled" in this context includes branching elements that branch from the elongate member (to form more than one elongate member). So when the elongate members are described as not being directly coupled to anything, that includes that the elongate members don't having any branching members that extend from the elongate member. Another way of describing that is the elongate member is a single elongate member from which a branching element does not extend, and the elongate member is not directly coupled, or attached, to another component.

In any of the embodiments herein, there can be two, three, four, five, six, seven, eight, nine, ten, or more expandable elongate members. There can be as many as can be included based on any particular design. In some embodiments there are from 2 and 30 expandable elongate members 111.

Each of the expandable elongate members 111, when expanded outward as shown, have a configuration that bows outward relative to an axis of shaft 131, then after reaching a max radially outward dimension, extends back radially inward toward the longitudinal axis of shaft 131, as shown. The height changes more quickly in the proximal portion of the device, and reduces more gradually on the distal side of the max height dimension, as shown.

At least one of the elongate members 111 carries at least one hook, barb, or other type of piercing element 113 (only 2 are labeled in FIG. 5) adapted to pierce LAA tissue and anchor the occlusion device relative to the tissue. The hooks or barbs can be integrally formed with any of the elongate members (i.e., made from the same starting material), and can be adapted to expand or change position relative to the elongate member upon release from a delivery device (e.g., expand further radially outward). The hooks can be the same material as the elongate members. They can also have different properties as the elongate materials, such as different thicknesses. They can be less flexible than the elongate members 111, for example.

Occlusion device 110 is adapted to be expanded with an inflatable balloon 120, rather than being self-expanding. Balloon 120 has a preformed shape (such as with a generally inelastic material) when inflated with a known volume. The balloon can be molded to have a shape that resembles typical LAAs. Balloon 120 has a generally tapering configuration, and can be generally cone or pear shaped. In some embodiments, the balloon is made of silicone, and is relatively thin. Balloon 120 can be carried by the distal end of delivery device 130, such as a delivery cable or shaft, and can be in fluid communication via a fluid lumen with a fluid source external to the patient, such as is described above with respect to FIGS. 1-4. In fact, the sealing steps and features from FIGS. 1-4 can be incorporated into the FIG. 5 embodiment if desired, potentially as an additional safety net during the procedure.

Once the device 110 and uninflated balloon are delivered through the existing sheath, the balloon is inflated, which pushes the expandable members 111 radially outward. In this embodiment, the plurality of elongate members are not self-expandable, but rather are balloon expandable. In other embodiments, they could be partially self-expandable, and further expanded with balloon 120. When expandable members 111 are urged radially outward, hooks 113 pierce through LAA tissue, securing the device 110 with respect to LAA tissue.

The balloon 120 can be inflated until the outermost dimension D (relative to a longitudinal axis) of the occlusion device 110 has reached a desired size. One advantage of device 110 is that it does not have a premade, expanded configuration, like a self-expanding device. It assumes a shape in situ when expanded by balloon 120. This allows the device to be a one-size fits all device, and it is expandable until it reaches the desired size, which can be confirmed by ensuring blood is not entering into the LAA from the left atrium, using any of techniques described herein. Generally, the device 110 is expanded until blood is not entering from the atrium into the LAA, and methods for assessing the same are described above and applicable in this embodiment.

Once the device 110 has sufficiently occluded the LAA, the balloon 120 is deflated, and the balloon and delivery device 130 are removed through a central region of occlusion device 110. Prior to removal, the delivery device is released from the device 110 using any of a number of attach and release mechanisms. For example, the delivery device can include a detachable connector pin to attach and release the occlusion device 110 from a delivery cable.

The central region can be thought of as a trap door, and may function similar to a one way valve through a central region of the device 110.

The plurality of elongate members 111 are secured to a material that extends between the elongate members and acts to occlude blood, similar to the Watchman device described above. The material extends across at least a proximal portion of the expandable device 110.

Figure 6:
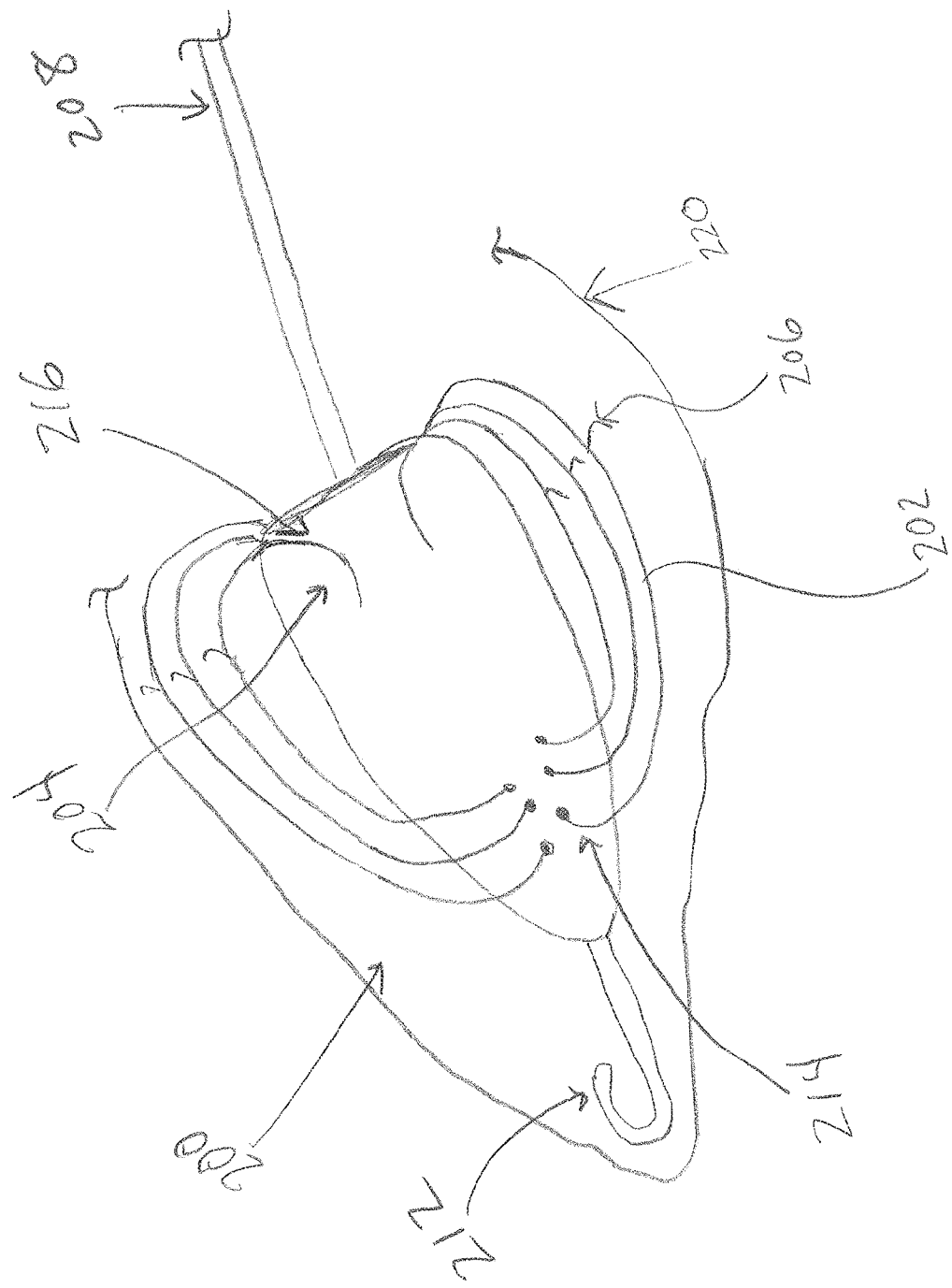
FIG. 6 shows an exemplary permanent implant adapted for occluding a LAA.

FIG. 6 illustrates another exemplary embodiment that is similar to the device shown in FIG. 5, and any suitable disclosure for FIG. 5 can be incorporated by reference with the example in FIG. 6 unless specifically indicated to the contrary. FIG. 6 illustrates an implantable LAA occlusion device 200, after it has been delivered to a position within a LAA. The implantable device includes a plurality of elongate elements, 202, which are similar to members 111 from FIG. 5. In this embodiment, however proximal end regions of the elongate elements include a folded, or bent, region 204. They can be bent backwards towards the distal end to some degree prior to expansion, or can be extending generally radially inward toward the longitudinal axis of the device prior to expansion. Each elongate member has an atraumatic distal end, such as a ball, curled region 214, etc., which minimizes damage to LAA tissue. The ends could even have, for example, pigtail configurations. The elongate elements 202 can include anchors 206 that can be in form of hooks or barbs, as did elongate members 11 from the example in FIG. 5. All of the disclosure regarding hooks or barbs from FIG. 5 can apply to anchors 206. Each of the elongate members 202 can have more than one anchor 206.

Device 200 is, like the device in FIG. 5, open ended at its distal end, and the entire disclosure from FIG. 5 about being open-ended and the elongate members not coupled directly to anything at their distal ends applies to the device in FIG. 6 as well.

The device in this embodiment can be delivered using a delivery and expansion device, which includes elongate shaft 208, which can have a flexible distal region with a pigtail configuration, but which can be straightened if being delivered "over the wire." The distal end of shaft 208 can also have one or more ports therein, which can be used as injections ports to assist with determining if there is a leakage between LAA and the atrium, similar to ports 37 from FIG. 3. The delivery device also includes balloon 210 mounted to shaft 208, which is pre-shaped and can function be just like balloon 120 from FIG. 5. The balloon is in fluid communication with a fluid lumen within elongate shaft 208.

An exemplary "over the wire" placement of the implantable device now follows. LAA wall 220 is shown in FIG. 6. If the access is transeptal, a wire can be placed in the LAA, and the septal sheath can still be in position extending across the septum. The implantable device, while secured to the placement and expansion device, can then be advanced over the wire that has already been placed. The wire can be removed, allowing the pigtail 212 to form a present an atraumatic distal end. The balloon can then be inflated as described above for FIG. 5, and can be continued to be inflated until it is believed that the elongate member and optional anchors are anchored to tissue. The barrier 216 secured to the proximal end regions of the elongate elements can begin to assume a larger configuration due to the elongate elements expanding. Optionally, the proximal regions of the elongate members that are bent backwards can be designed so that as the device is expanded, the proximal end regions deform and begin to extend more directly radially inward, together forming a somewhat flattened proximal end of the implant, across which the barrier extends. The expansion process can thus allow the proximal ends to deform and create a proximal end of the expandable portion of the implant device.

The shaft 208 can have ports distal to the balloon 210 that can be used to inject dye to check if fluid is leaking from within the LAA to a location in the atrium. If it is, the balloon can be inflated more, and leakage can then be rechecked. The process can be continued until no leakage is detected, and the device is determined to have been expanded sufficiently.

The balloon 210 can then be deflated, and removed through a central opening in the proximal region of the implantable device. The bent back regions 204 can be adapted so that when the balloon is deflated, the bent back regions 204 can also revert so that they are extending in a more radially inward configuration, helping create the barrier configuration of the proximal end of the implantable device. Optionally still, the proximal bent back regions 204 of the elongate members 202 can be adapted so that as the balloon and delivery device 208 are retracted proximally, the bent back regions 204 can continue to deform so they extend radially inward. In still further embodiments, the proximal regions 204 are adapted to interact with one another as they revert to the different configuration, and can lock together or at least become more stabilized relative to one another.

Any of the elongate members in FIGS. 5 and 6, even though they may have a curved configuration in a side view of the elongate member from a proximal end to a distal end, can also have linear configurations when viewed 90 in a top or bottom view. This is shown in both FIGS. 5 and 6.

The invention claimed is:

1. A method of occluding a left atrial appendage ("LAA), comprising:
   delivering an inflatable member that is carried by an elongate member to the LAA;
   inflating the inflatable member against one or more of LAA tissue, LAA ostium tissue, or left atrium tissue adjacent a LAA ostium, wherein inflating the inflatable member does not cause expansion of an implant;
   wherein inflating the inflatable member comprises delivering a predetermined volume of inflation fluid into the inflatable member to inflate the inflatable member
   at a time subsequent to expanding the inflatable member, injecting a dye from the elongate member into the patient; and
   determining if the dye is flowing between a location that is outside of the LAA and the LAA.

2. The method of claim 1, wherein delivering the inflatable member comprises advancing the inflatable member through a lumen of an access sheath that was previously positioned in the left atrium as part of a procedure attempting to deliver a LAA implantable device.

3. The method of claim 1, further comprising sealing a ruptured opening in LAA tissue.

4. The method of claim 3, wherein sealing a ruptured opening in the LAA comprises injecting a sealant into the LAA to seal off the ruptured opening in the LAA.

5. The method of claim 1 wherein inflating the inflatable member comprises temporarily inflating the inflatable member.

6. The method of claim 1, wherein inflating the inflatable member comprises inflating the inflatable member until it assumes a pre-set configuration.

7. The method of claim 1, further comprising advancing a curved distal member of the elongate member into the LAA until resistance is felt.

8. The method of claim 1, further comprising, at a time subsequent to determining if the dye is flowing between a location that is outside of the LAA and the LAA, deflating the inflatable member and removing it from the patient.

9. A method of occluding a left atrial appendage ("LAA), comprising:
   delivering an inflatable member that is carried by an elongate member to the LAA;
   inflating the inflatable member against one or more of LAA tissue, LAA ostium tissue, or left atrium tissue adjacent a LAA ostium without expanding an implant;
   at a time subsequent to expanding the inflatable member, injecting a dye from the elongate member into the patient;
   determining if the dye is flowing between a location that is outside of the LAA and the LAA; and
   sealing a ruptured opening in the LAA by injecting a sealant into the LAA to seal off the ruptured opening in the LAA.

* * * * *